United States Patent
Gao et al.

(10) Patent No.: US 9,955,861 B2
(45) Date of Patent: May 1, 2018

(54) CONSTRUCTION OF AN INDIVIDUAL EYE MODEL USING A PLENOPTIC CAMERA

(71) Applicants: Liang Gao, Santa Clara, CA (US); Ivana Tosic, San Francisco, CA (US)

(72) Inventors: Liang Gao, Santa Clara, CA (US); Ivana Tosic, San Francisco, CA (US)

(73) Assignee: Ricoh Company, Ltd., Tokyo (JP)

( * ) Notice: Subject to any disclaimer, the term of this patent is extended or adjusted under 35 U.S.C. 154(b) by 0 days. days.

(21) Appl. No.: 15/063,254

(22) Filed: Mar. 7, 2016

(65) Prior Publication Data

US 2017/0105615 A1    Apr. 20, 2017

Related U.S. Application Data

(60) Provisional application No. 62/242,679, filed on Oct. 16, 2015.

(51) Int. Cl.

| | |
|---|---|
| A61B 3/14 | (2006.01) |
| A61B 3/00 | (2006.01) |
| A61B 3/10 | (2006.01) |
| A61B 3/107 | (2006.01) |
| A61B 3/117 | (2006.01) |
| A61B 3/15 | (2006.01) |
| G06T 7/557 | (2017.01) |

(52) U.S. Cl.
CPC ............ *A61B 3/0025* (2013.01); *A61B 3/107* (2013.01); *A61B 3/1015* (2013.01); *A61B 3/1173* (2013.01); *A61B 3/158* (2013.01); *A61B 3/14* (2013.01); *G06T 7/557* (2017.01)

(58) Field of Classification Search
CPC ............ A61B 3/14; A61B 3/103; A61B 3/107

USPC ........................................................ 351/206
See application file for complete search history.

(56) References Cited

U.S. PATENT DOCUMENTS

| | | | |
|---|---|---|---|
| 4,658,372 | A | 4/1987 | Witkin |
| 6,711,293 | B1 | 3/2004 | Lowe |
| 6,954,202 | B2 | 10/2005 | Han et al. |
| 7,199,793 | B2 | 4/2007 | Oh et al. |
| 7,382,897 | B2 | 6/2008 | Brown et al. |
| 8,244,058 | B1 | 8/2012 | Lntwala et al. |

(Continued)

FOREIGN PATENT DOCUMENTS

| | | |
|---|---|---|
| EP | 3020326 A2 | 5/2016 |
| JP | 2004-321508 A | 11/2004 |

(Continued)

OTHER PUBLICATIONS

European Extended Search Report, European Application No. 16189041.3, dated Mar. 21, 2017, 7 pages.

(Continued)

*Primary Examiner* — Mahidere Sahle
(74) *Attorney, Agent, or Firm* — Fenwick & West LLP

(57) ABSTRACT

A single imaging platform for making in vivo measurements of an individual's eye, where the measurements are sufficient to construct an optical model of the individual's eye. The platform includes a plenoptic opthalmic camera and an illumination module. In one configuration, the plenoptic opthalmic camera captures a plenoptic image of a corneal anterior surface of the individual's eye. In another configuration, the plenoptic opthalmic camera operates as a wavefront sensor to measure a wavefront produced by the individual's eye.

20 Claims, 7 Drawing Sheets

(56) References Cited

U.S. PATENT DOCUMENTS

| | | | |
|---|---|---|---|
| 8,315,476 | B1 | 11/2012 | Georgiev et al. |
| 8,941,750 | B2 | 1/2015 | Yamamoto |
| 9,460,515 | B2 | 10/2016 | Tosic et al. |
| 2008/0219579 | A1 | 9/2008 | Aksyuk et al. |
| 2011/0032337 | A1 | 2/2011 | Rodriguez Ramos et al. |
| 2011/0069189 | A1 | 3/2011 | Venkataraman et al. |
| 2012/0050562 | A1 | 3/2012 | Perwass et al. |
| 2013/0128068 | A1 | 5/2013 | Georgiev et al. |
| 2014/0268044 | A1 | 9/2014 | Copland |
| 2015/0117756 | A1 | 4/2015 | Tosic et al. |
| 2016/0005228 | A1* | 1/2016 | Niebla, Jr. ......... H04N 13/0022 348/43 |
| 2016/0135680 | A1* | 5/2016 | Anderson ............ A61B 3/0025 351/206 |

FOREIGN PATENT DOCUMENTS

| | | |
|---|---|---|
| JP | 2010-263353 A | 11/2010 |
| JP | 2012-521237 A | 9/2012 |
| JP | 2013-175948 A | 9/2013 |
| JP | 2014-106970 A | 6/2014 |
| JP | 2015-084223 A | 4/2015 |
| JP | 2015-521926 A | 8/2015 |
| WO | WO 2010/109020 A1 | 9/2010 |

OTHER PUBLICATIONS

Liang, J., et al., "Objective Measurement of Wave Aberrations of the Human Eye with the User of a Hartmann-Shack Wave-Front Sensor," J. Opt. Soc. Am. A, Jul. 1994, pp. 1949-1957, vol. 11, No. 7.
Jain, R., Pentacam: Principle and Clinical Applications,: Journal of Current Glaucoma Practice, May-Aug. 2009, pp. 20-32, vol. 3, No. 2.
Pamplona, V.F. et al., "NETRA: Interactive Display for Estimating Refractive Errors and Focal Range," ACM SIGGRAPH '10, Article 77, 2010, 9 pages.
Kim, C. et al. "Scene Reconstruction from High Spatio-Angular Resolution Light Fields," Transactions on Graphics (TOG), Jul. 2013, 11 pages, vol. 32, No. 4.
Lindeberg, T., "Edge Detection and Ridge Detection with Automatic Scale Selection," IEEE Computer Society Conference on in Computer Vision and Pattern Recognition, Proceedings CVPR '96, IEEE 1996, 1996, pp. 465-470.
Lindeberg, T., "Generalized Gaussian Scale-Space Axiomatics Comprising Linear Scale-Space, Affine Scale-Space and Spatio-Temporal Scale-Space," Journal of Mathematical Imaging and Vision, 2011, pp. 36-81, vol. 40, No. 1.
Lindeberg, T., "Scale-Space," Wiley Encyclopedia of Computer Science and Engineering, 2008, 2495-2504, May be retrieved at<URL:http://onlinelibrary.wiley.com/doi/10.1002/9780470050118.ecse60-9/abstract.
Lowe, D. G., "Distinctive Image Features From Scale-Invariant Keypoints," International Journal of Computer Vision, 2004, pp. 91-110, vol. 60, No. 2.
Seitz, S. M. et al., "A Comparison and Evaluation of Multi-View Stereo Reconstruction Algorithms," Proceedings of the 2006 IEEE Computer Society Conference on Computer Vision and Pattern Recognition (CVPR'06), IEEE, 2006, pp. 519-528, vol. 1.
Wanner, S. et al., "Globally Consistent Depth Labeling of 4d light Fields," 2012 IEEE Conference on Computer Vision and Pattern Recognition (CVPR), IEEE, 2012, pp. 41-48.
Witkin, A., "Scale-Space Filtering: A New Approach to Multi-Scale Description," IEEE International Conference on Acoustics, Speech, and Signal Processing, ICASSP'84, IEEE, 1984, pp. 150-153, vol. 9.
European Extended Search Report, European Application No. 14187353.9, Oct. 29, 2015, 12 pages.
Feris, R.S., "Detection and Modeling of Depth Discontinuities with Lighting and Viewpoint Variation," PhD Thesis, 2006, pp. 1-165, [Online] [Retrieved on Oct. 21, 2015], May be retrieved at<URL:http://www.cs.ucsb.edu/mturk/pubs/FerisPhD.pdf>.
Gortler, S.J. et al., "The Lumigraph," Computer Graphics Proceedings 1996 (SIGGRAPH), Aug. 7, 1996, pp. 43-54.
Lin, Y. et al., "Occlusion-Aware Layered Scene Recovery from Light Fields," 2013 IEEE International Conference on Image Processing, Sep. 15, 2013, pp. 295-299.
Lindeberg, T. et al., "Feature Detection with Automatic Scale Selection," International Journal of Computer Vision, Nov. 1998, pp. 79-116, vol. 30, No. 2.
Tosic, I. et al., "Light Field Scale depth Space Transform for Dense Depth Estimation," 2014 IEEE Conference on Computer Vision and Pattern Recognition Workshops, IEEE, Jun. 23, 2014, pp. 441-448.
Tosic, I. et al., "3D Keypoint Detection by Light Field Scale-Depth Space Analysis," 2014 IEEE International Conference on Image Processing (ICIP), Oct. 2014, pp. 1927-1931.
Wanner, S. et al., "Globally Consistent Depth Labeling of 4D Light Fields," 2012 IEEE Conference on Computer Vision and Pattern Recognition (CVPR), Jun. 16, 2012, pp. 41-48.
Japanese Office Action, Japanese Application No. 2016-202553, dated Oct. 3, 2017, 5 pages (with concise explanation of relevance).

\* cited by examiner

CONSTRUCTION OF AN INDIVIDUAL EYE MODEL USING A PLENOPTIC CAMERA

CROSS-REFERENCE TO RELATED APPLICATION(S)

This application claims priority under 35 U.S.C. § 119(e) to U.S. Provisional Patent Application Ser. No. 62/242,679, "Construction of an Individual Eye Model Using a Plenoptic Fundus Camera," filed Oct. 16, 2015. The subject matter of all of the foregoing is incorporated herein by reference in its entirety.

BACKGROUND

1. Field of the Invention

This invention relates generally to measurement of the eye and construction of eye models based on such measurements.

2. Description of Related Art

In the past decades, a variety of generic optical models for the human eye have been established to facilitate the diagnosis and treatment of ocular diseases. However, as a complicated imaging system, each individual eye has its own physiological characteristics. Characterizing the optical parameters of an individual eye is crucial for applications such as assessing wound healing after corneal refractive surgery and optimizing eye glasses or contact lenses.

To construct an individual eye model, typically three ocular surfaces are modeled: the anterior surface of cornea, which is responsible for ~70% optical power of the eye, and the anterior and posterior surfaces of the crystalline lens, which are responsible for the remaining ~30% optical power of the eye. The individual eye model can be established in vivo by combining three techniques: corneal topography, wavefront aberration measurement, and numerical modeling. Conventionally, the corneal surface curvature is acquired by either using a Placido disc (e.g., Zeiss ATLAS corneal topography system), or using a scanning slit (e.g., Orbscan corneal topographer), or Scheimpflug photography (e.g., Pentacam corneal topographer). The wavefront aberration is typically measured using a Hartmann-Shack sensor (e.g., Zeiss i.Profiler wavefront analyzer). However, the reliance on multiple costly instruments limits the accessibility of constructing an individual eye model to the general ophthalmologists. In addition, because the conventional corneal topography techniques rely on scanning, 1-2 seconds are typically required in order to complete the measurement. The movement of the eye during this process may introduce motion artifacts.

In addition, plenoptic imaging can be used to estimate depth based on disparity measurements. However, in plenoptic three-dimensional imaging, a prior disparity-to-depth calibration is generally required in order to reconstruct the objects' depths. Typically during calibration, a grid or point target is placed in front of the plenoptic imaging system and scanned along one axis (in case of grid target) or three spatial axes (in case of point target). However, when imaging the eye, such a procedure cannot be used because the eye's crystalline lens is also a part of the imaging system and we cannot simply put a target with "known" depth inside the individual's eye.

Thus, there is a need for better approaches to making eye measurements used to construct an individual eye model.

SUMMARY

The present disclosure overcomes the limitations of the prior art by providing a single imaging platform for making in vivo measurements of an individual's eye, where the measurements are sufficient to construct an optical model of the individual's eye. The platform includes a plenoptic ophthalmic camera and an illumination module. In a first configuration of the imaging platform, the plenoptic ophthalmic camera captures in vivo a plenoptic image of a corneal anterior surface of the individual's eye. In a second configuration, the plenoptic ophthalmic camera operates as a wavefront sensor to measure in vivo a wavefront produced by light propagating through the individual's eye. The optical model of the individual's eye is generated based on the captured plenoptic image and the measured wavefront.

Other aspects include components, devices, systems, improvements, methods, processes, applications, computer readable mediums, and other technologies related to any of the above.

BRIEF DESCRIPTION OF THE DRAWINGS

Embodiments of the disclosure have other advantages and features which will be more readily apparent from the following detailed description and the appended claims, when taken in conjunction with the accompanying drawings, in which:

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Figure 1:
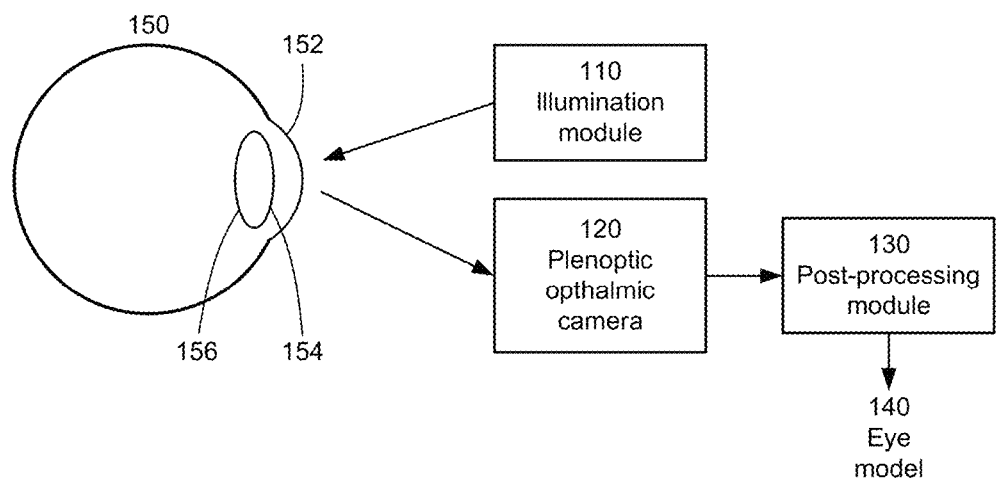
FIG. 1 illustrates an imaging platform, according to an embodiment.

FIG. 1 illustrates an imaging platform that can implement both corneal topography and wavefront aberration measurement using a single instrument—a plenoptic ophthalmic camera 120—and can generate a complete eye model 140 of an individual through a post-processing module 130. The imaging platform includes an illumination module 110 and a plenoptic ophthalmic camera 120. The illumination module 110 illuminates the individual's eye 150 and the plenoptic ophthalmic camera 120 makes measurements of the eye as illuminated. A post-processing module 130 (e.g., a computer system) accesses these measurements to generate an optical model of the individual's eye. The eye model 140 preferably includes optical models of the corneal anterior surface 152, of the lens anterior surface 154, and of the lens posterior surface 156.

In a first configuration of the imaging platform, the plenoptic ophthalmic camera 120 captures in vivo a plenoptic image of a corneal anterior surface of the individual's eye. In a second configuration, the plenoptic ophthalmic camera operates as a wavefront sensor to measure in vivo a wavefront produced by light propagating through the individual's eye. The optical model of the individual's eye is generated based on the captured plenoptic image and the measured wavefront.

In one implementation of the first configuration, the illumination module illuminates the corneal anterior surface with a predefined pattern, and the plenoptic ophthalmic camera captures the plenoptic image of the corneal anterior surface as illuminated by the predefined pattern. The captured plenoptic image provides sufficient data to construct an optical model of the corneal anterior surface of the individual's eye, for example by generating a depth map of the corneal anterior surface from the disparity in the plenoptic image.

In one implementation of the second configuration, the illumination module produces a point image on a retina of the individual's eye, and the plenoptic ophthalmic camera operates as a wavefront sensor to measure in vivo the wavefront produced by the point image reflected from the retina of the individual's eye. In this case, the plenoptic system images the pupil of the eye in order to measure the wavefront. The wavefront measurement is used to construct optical models of the lens anterior surface and of the lens posterior surface of the individual's eye. For example, a computer simulation of the individual's eye can be created. The corneal anterior surface can be modeled based on results from the first configuration measurements. The computer simulation is used to simulate a wavefront produced by the individual's eye. The optical models for the lens anterior surface and for the lens posterior surface are optimized to reduce a difference between the simulated wavefront and the measured wavefront.

Figure 2A:
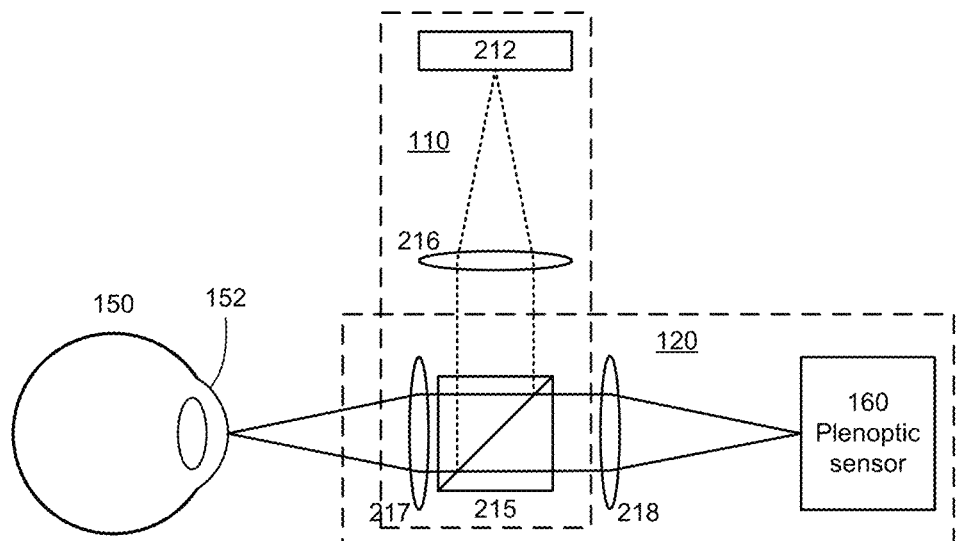
FIGS. 2A-2B illustrate an imaging platform configured for plenoptic imaging and for wavefront measurement, respectively, according to an embodiment.
Figure 2B:
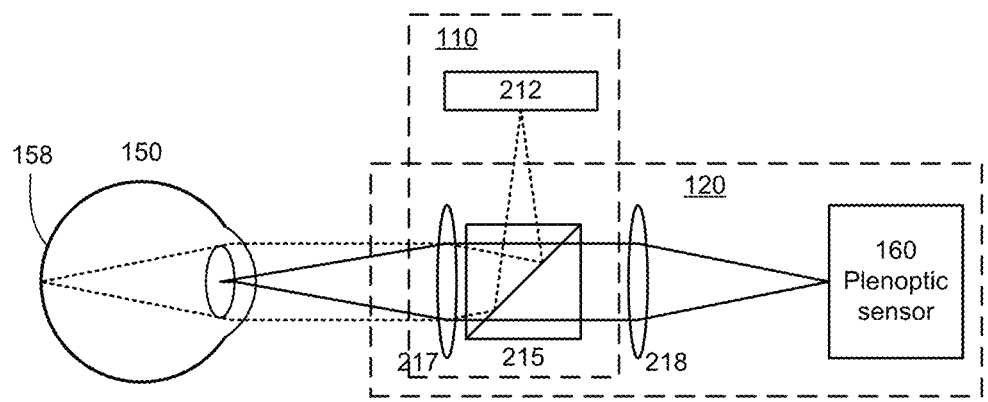

The platform can be configured for two different modes, as illustrated in FIGS. 2A-2B. In this example, the illumination module 110 includes an illumination source such as an electronic display screen 212 (LED or OLED). The imaging platform also includes a polarization beamsplitter 215 and relay lenses, which are used to overlap the optical paths for the illumination module 110 and the plenoptic ophthalmic camera 120. This allows simultaneous illumination by the illumination module 110 and acquisition of measurements by the plenoptic ophthalmic camera 120.

In FIG. 2A, a predefined pattern, such as a grid pattern, is displayed on the electronic display 212. The grid pattern is relayed through a 4f lens system 216-217 and illuminates the corneal anterior surface 152 of the individual's eye 150. In this example, the beamsplitter 215 rejects the specularly reflected light from the cornea and allows only the scattered light to pass through. The plenoptic ophthalmic camera 120 captures a plenoptic image of the illuminated cornea 152, which is imaged by the 4f lens system 217-218 onto the plenoptic sensor 160 (e.g., a microlens array in combination with a sensor array), preferably in a single snapshot. The plenoptic image inherently includes multiple images of the corneal anterior surface 152 captured from multiple different viewpoints. These different viewpoints can be processed to produce a depth map of the object, as will be described in more detail below.

In FIG. 2B, a point object is displayed on the electronic display 212. The light from this point source is collimated by an achromatic lens 217 and focused onto the retina 158 of the individual's eye 150, thus producing a point image on the retina. The point image effectively operates as a point source located on the retina 158. The resulting wavefront is a measurement of the effect of the different surfaces within the eye. The plenoptic ophthalmic camera 120 operates as a wavefront sensor by imaging the pupil of the eye in order to measure the wavefront produced by the point image reflected from the retina 158. The wavefront emitted from the eye is relayed through a 4f system 217-218 to the plenoptic sensor 160 operating as a wavefront sensor.

Between the two modes shown in FIGS. 2A-2B, the plenoptic ophthalmic camera 120 captures a plenoptic image of the corneal anterior surface 152 and also captures a wavefront measurement of a wavefront produced by a point source on the retina 158. The post-processing module 130 accesses these two measurements and processes them to generate the optical models of the three eye surfaces.

Figure 3:
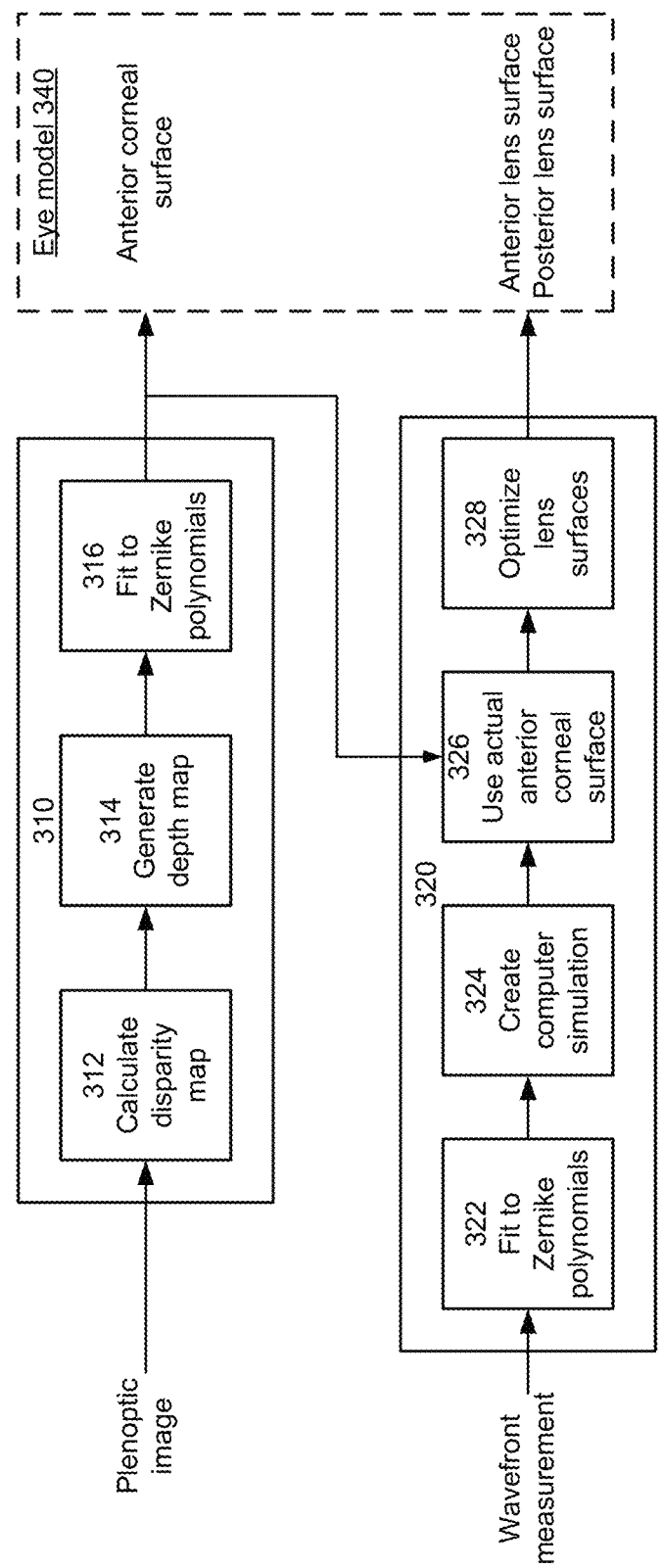
FIG. 3 illustrates a process for post-processing measurements to generate an optical model of an individual's eye, according to an embodiment.

FIG. 3 illustrates an example of this process. At a high level, the optical model for the corneal anterior surface 152 is generated 310 based on the captured plenoptic image, and the optical model for the anterior and posterior lens surfaces 154, 156 are generated 320 based on the measured wavefront. The eye model 340 for an individual includes the optical models for these three surfaces.

FIG. 3 also illustrates a more specific example for each step 310, 320. In the example of step 310, the corneal topography is determined as follows. A disparity map is calculated 312 from the plenoptic image. There is a one-to-one mapping between disparity and depth, which can be determined by calibration, for example. Accordingly, the disparity map is used to generate 314 a corresponding depth map for the cornea 152. Examples of plenoptic image three-dimensional reconstruction are described in further detail below and in U.S. patent application Ser. No. 14/064,090, "Processing of Light Fields by Transforming to Scale and Depth Space," which is incorporated herein by reference. In this example, the depth map for the corneal anterior surface is fitted 316 into Zernike polynomials in the form:

$$Z = \frac{cr^2}{1+\sqrt{1-(1+k)c^2r^2}} + \sum_{i=1}^{N} A_i Z_i(r, \varphi), \tag{1}$$

where c is the curvature of the surface, r is the radial coordinate in lens units, k is the conic constant, $A_i$ is the coefficient on the $i^{th}$ Zernike polynomial, N is the number of Zernike coefficients in the series, and $Z_i$ (r, $\varphi$) are Zernike terms and associated with different wavefront aberrations. Note that for reconstruction of the corneal anterior surface, the optical system does not include the eye lens. Thus, the plenoptic ophthalmic camera can be pre-calibrated for the disparity-to-depth mapping, for example as described in U.S. patent application Ser. No. 15/050,422, "Disparity-to-Depth Calibration for Plenoptic Imaging Systems," which is incorporated herein by reference.

In the example of step 320, the plenoptic ophthalmic camera is used as a Hartmann-Shack sensor. A point object on the electronic display is focused onto the patient's retina. The patient may be asked to make adjustments in order to sharpen the point image that he sees. The scattered light's wavefront emitting from the eye is imaged by the plenoptic ophthalmic camera. The image typically looks like an array of slightly offset points, with each point representing the local slope of the wavefront. The captured image is converted to a wavefront function using standard techniques. The measured wavefront error, W, is fitted 322 to Zernike polynomials in the form:

$$W = \sum_{i=1}^{N} B_i Z_i(r, \varphi). \quad (2)$$

Here $B_i$ is the coefficient on the $i^{th}$ Zernike polynomial, N is the number of Zernike coefficients in the series, and $Z_i(r, \varphi)$ are Zernike terms. The Zernike representation is useful because it is a good basis set for optical wavefronts and because it can be expressed in a format that is suitable for use with optical design software, such as Zemax or CodeV.

A computer simulation of the individual eye is created 324. In this example, the computer simulation begins with a generic eye model (e.g., the Arizona eye model) implemented on optical design software. In general, the Arizona eye model matches the on- and off-axis aberration levels that have been determined based on average clinical data. To customize this standard model, the corneal anterior surface from the standard model is replaced 326 by the actual surface calculated in step 310. The lens anterior and posterior surfaces are represented by Zernike standard sag surface types, with the Zernike coefficients set as variables for optimization.

The computer simulation of the individual eye can then be used to simulate the wavefront produced by the individual's eye. A merit function based on the difference between the simulated and measured wavefronts is defined. The wavefronts preferably are defined at a plane tangent to the corneal anterior surface and perpendicular to the optical axis. The Zernike coefficients for the lens anterior and posterior surfaces are optimized 328 based on improving the merit function (i.e., reducing the difference between the simulated and measured wavefronts). The result is a model of the individual's eye that includes optical models of the corneal anterior surface, of the lens anterior surface, and of the lens posterior surface, which are the three surfaces that account for the vast majority of optical power in an eye.

Figure 4A:
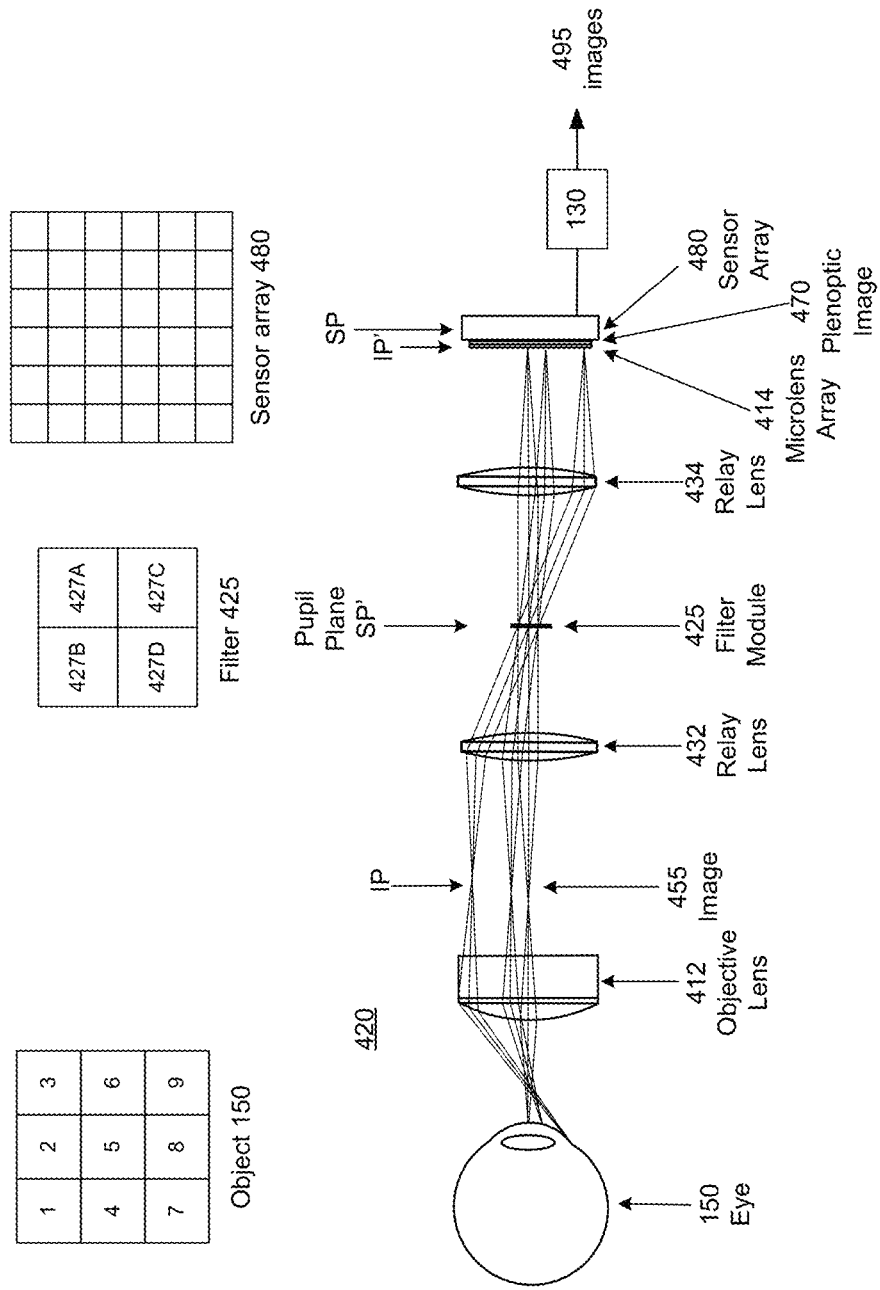
FIGS. 4A-4B illustrate an example of a plenoptic ophthalmic camera, according to an embodiment.
Figure 4B:
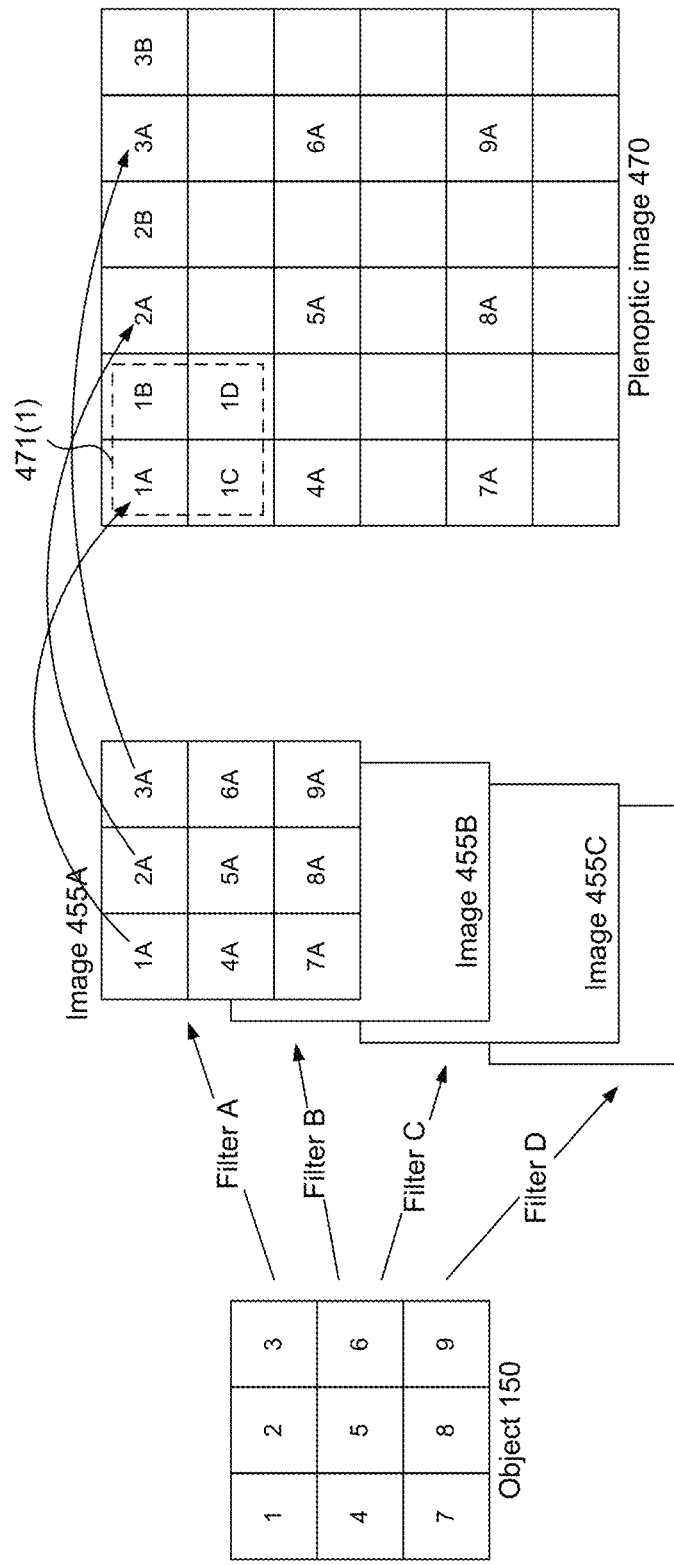
Figure 5:
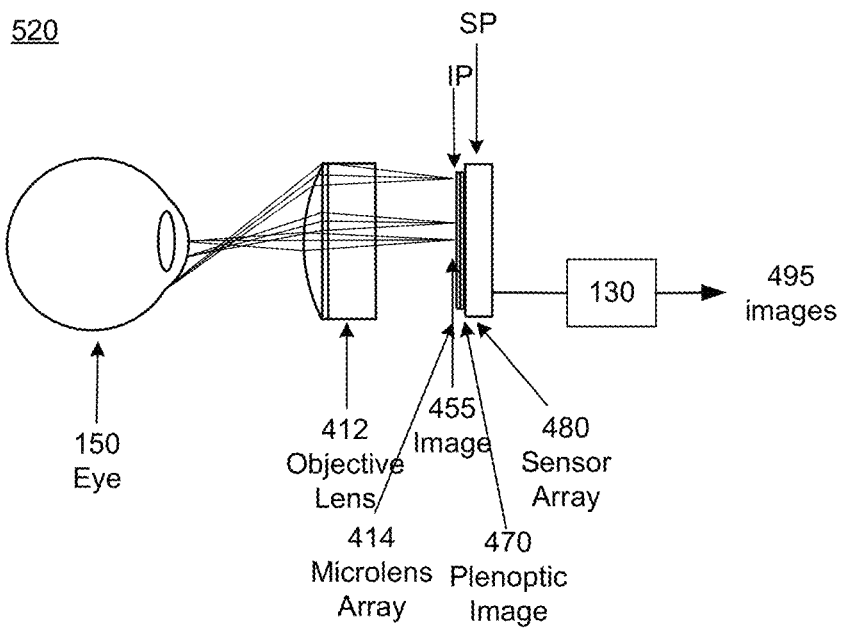
FIG. 5 illustrates another example of a plenoptic ophthalmic camera, according to an embodiment.

FIGS. 4-5 illustrate examples of plenoptic ophthalmic cameras. In FIGS. 4A-4B, the plenoptic ophthalmic camera 420 includes an objective lens 412 (represented by a single lens in FIG. 4A), a secondary imaging array 414 (an array of image forming elements) and a sensor array 480. For convenience, the imaging optics 412 is depicted in FIG. 4A as a single optical element, but it should be understood that it could contain multiple elements. The implementation of FIG. 4A also includes a set of relay lenses 432, 434.

The secondary imaging array 414 may be referred to as a microimaging array. The secondary imaging array 414 and sensor array 480 together may be referred to as a plenoptic sensor or plenoptic sensor module. In this example, the secondary imaging array 414 is a microlens array. Other examples of microimaging arrays 414 include microlens arrays, arrays of pinholes, micromirror arrays, checkerboard grids and waveguide/channel arrays. The microimaging array 414 can be a rectangular array, hexagonal array or other types of arrays.

These components form two overlapping imaging subsystems. In the first imaging subsystem, the objective lens 412 is positionable in front of the individual's eye 150 and forms an optical image 455 of the eye (retina, in this example) at the primary image plane IP, which is relayed to conjugate planes such as the image port IP'. This imaging subsystem has a pupil plane. In the second imaging subsystem, the secondary imaging array 414 images the pupil plane onto the sensor array 480. To do this, the microimaging array 414 is located at the image plane IP or one of its conjugate planes, so that the pupil plane is now located at a conjugate SP' to the sensor plane SP. In this example, the microlens array 414 is located at conjugate plane IP'. The system in its entirety forms at the sensor plane SP a plenoptic image 470, which includes spatially multiplexed and interleaved optical images.

A filter module 425 may optionally be positioned at a plane SP' conjugate to the sensor plane SP. The actual physical location may be before, after or in the middle of the imaging optics 412. The filter module contains a number of spatially multiplexed filters 427A-D. In this example, the filter module 425 includes a rectangular array of filters 427, as shown in the top portion of FIG. 4A. The filter module 425 could contain spectral filters, polarization filters, neutral density filters, clear filters (i.e., no filters) or combinations of these.

The top portion of FIG. 4A provides more detail. In this diagram, the object 150 (e.g., the corneal anterior surface) is divided into a 3×3 array of regions, which are labeled 1-9. The filter module 425 is a 2×2 rectangular array of individual filters 427A-D. For example, each filter 427A-D may have a different spectral response. The sensor array 480 is shown as a 6×6 rectangular array.

FIG. 4B illustrates conceptually how the spatially multiplexed optical images 470A-D are produced and interleaved at sensor array 480. The object 150, if captured and filtered by filter 427A, would produce an optical image 455A. To distinguish filtered optical image 455A from an unfiltered image of the object, the 3×3 regions are labeled with the suffix A: 1A-9A. Similarly, the object 150 filtered by filters 427B,C,D, would produce corresponding optical images 455B,C,D with 3×3 regions labeled 1B-9B, 1C-9C and 1D-9D. Each of these four optical images 455A-D is filtered by a different filter 427A-D within filter module 425 but they are all produced simultaneously by the plenoptic imaging system 420. This allows different modality images and viewpoints to be captured in a single snapshot, eliminating the need to later compensate for eye movement when registering images.

The four optical images 455A-D are formed in an interleaved fashion at the sensor plane, as shown in FIG. 4B. Using image 455A as an example, the 3×3 regions 1A-9A from optical image 455A are not contiguous in a 3×3 block within optical image 470. Rather, regions 1A, 1B, 1C and 1D, from the four different optical images, are arranged in a 2×2 fashion in the upper left of optical image 470 (the inversion of image 470 is neglected for clarity). Regions 1-9 are similarly arranged. Thus, the regions 1A-9A that make up optical image 470A are spread out across the plenoptic image 470, separated by portions of the other optical images 470B-D. Put in another way, if the sensor is a rectangular array of individual sensor elements, the overall array can be divided into rectangular subarrays 471(1)-(9) of sensor elements (only one subarray 471(1) is shown in FIG. 4B). For each region 1-9, all of the corresponding regions from each filtered image are imaged onto the subarray. For example, regions 1A, 1B, 1C and 1D are all imaged onto subarray 471(1). Note that since the filter module 425 and sensor array 480 are located in conjugate planes, each imaging element in array 414 forms an image of the filter module 425 at the sensor plane SP. Since there are multiple imaging elements, multiple images 471 of the filter module 425 are formed.

The plenoptic image 470 is processed by processing module 130 to reconstruct desired images of the object. The processing could be deinterleaving and demultiplexing. It could also include more sophisticated image processing, such as the depth map construction described above. In addition to experiencing different filtering, the image data captured by plenoptic ophthalmic camera 420 also reflects different viewpoints. That is, the multiplexed images are captured from different viewpoints. This information can be used to reconstruct a three-dimensional image of the corneal anterior surface 150. Thus, the reconstructed images 495 can include three-dimensional information in addition to filtered images (e.g., color and/or polarization images). The system could be designed so that it is switchable between a depth mode and a multi-filter mode. Alternately, the system can capture both depth and spectral/polarization information simultaneously.

It should be noted that FIG. 4 has been simplified to illustrate underlying concepts. For example, the object 150 was artificially divided into an array in order to more easily explain the overall imaging function. As another example, most practical systems will use significantly larger arrays, particularly at the sensor array and possibly also at the filter module. In addition, there need not be a 2:1 relationship between the 6×6 regions at the sensor plane and the underlying sensor elements in the sensor array. Each region could correspond to multiple sensor elements, for example. As a final example, the regions labeled 1 in the object, 1A in the filtered image 455A and 1A in the plenoptic image 470 do not have to be exact images of each other. In some designs, region 1A within plenoptic image 470 may capture the filtered energy approximately from region 1 in the object 150, but it may not actually be an image of region 1. Thus, the energy collected by sensor elements in region 1A of plenoptic image 470 may be integrating and sampling the image (or some transformation of the image) in region 1 of object 150, rather than representing a geometrical reproduction of the object at that region. In addition, effects such as parallax, vignetting, diffraction and optical propagation may affect image formation.

FIG. 5 illustrates another example of a plenoptic ophthalmic camera, according to an embodiment. In this example, the microlens array 414 is positioned directly at the image plane IP rather than at one of its conjugates.

The following are some design considerations for corneal topography using a plentopic camera. Since the cornea is a reflectance object, the surface slope will deviate the incident chief rays and introduce relatively large reflectance angles. In order to collect the reflected light, the front optics must have a relatively large numerical aperture (NA). For example, given a 3 mm diameter field of view (FOV) on the cornea and 0 degree incident chief ray angle, the reflected chief ray will have a reflectance angle of 0.24 radians with respect to the optical axis. To collect this reflected chief ray, the front optics of the plentopic ophthalmic camera must have a NA larger than 0.24. To meet this requirement, we used a microscope objective with a 0.25 NA as shown in FIG. 2B. In addition, the desired lateral resolution for corneal imaging is around 100 μm or less and the desired depth resolution is around 50 μm or less.

Figure 6:
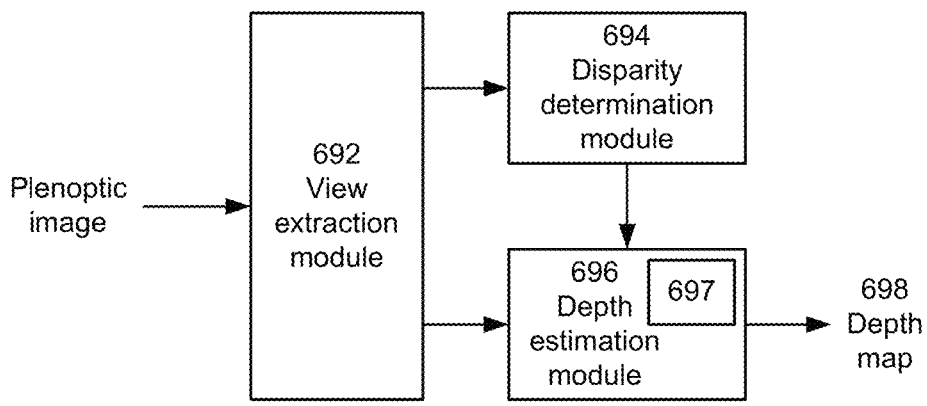
FIG. 6 illustrates a post-processing module that estimates depth, according to an embodiment.
Figure 7A:
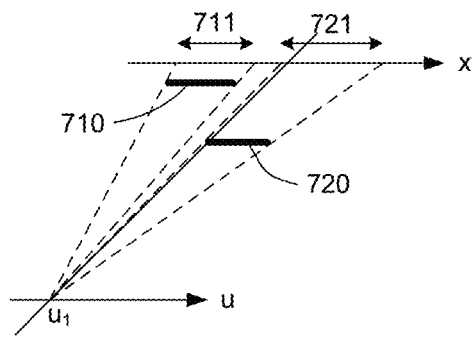
FIGS. 7A-7C illustrates two objects viewed from three different viewpoints.
Figure 7B:
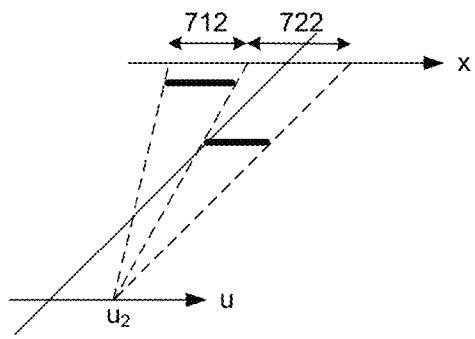
Figure 7C:
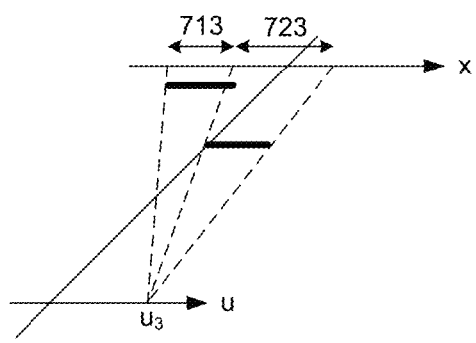
Figure 7D:
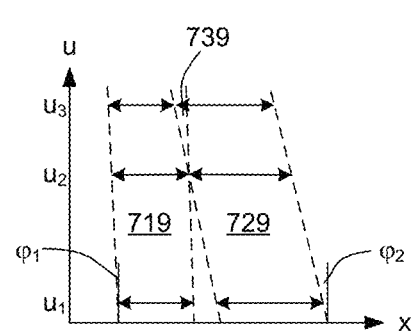
FIG. 7D illustrates an (x,u) slice of the corresponding light field, according to an embodiment.
Figure 8:
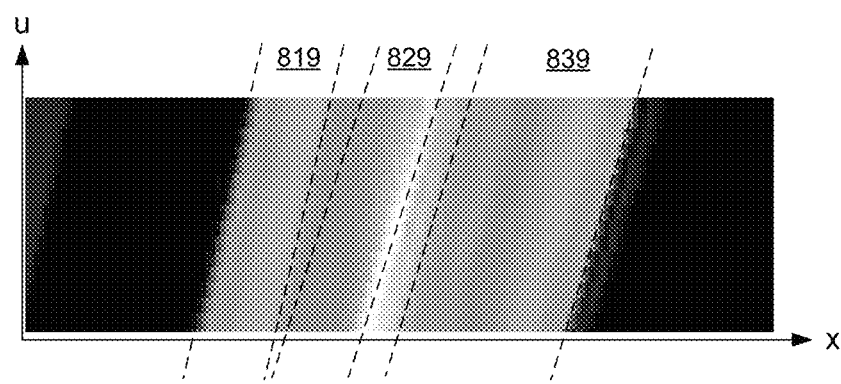
FIG. 8 illustrates ray regions superimposed on an (x,u) slice from a light field for a grayscale scene, according to an embodiment.

FIGS. 6-8 illustrate examples of determining a depth map for the corneal anterior surface (e.g., step 314 in FIG. 3). FIG. 6 illustrates one implementation of post-processing module 130 that estimates depth. In this example, the plenoptic image of the cornea is received by a view extraction module 692, which separates the sensor data into separate images 455 (or views), as described previously in FIG. 4B. These views are shifted relative to each other. That is, they exhibit disparity. Preferably, the disparity from one view to the next is less than one pixel. That is, the view-to-view disparity is sub-pixel. Disparity determination module 694 calculates the disparity. For example, it may do this by comparing corresponding features in different views 455. Alternately, module 694 may obtain the disparity from other sources. Depth estimation module 696 estimates the depth across the object by mapping the disparity from module 694 to corresponding depth. It uses a disparity-depth mapping 697 to do this. In one implementation, the mapping 697 between depth and disparity is the result of a calibration process. The output of module 696 is a depth map 698 that estimates the depth to different points on the anterior corneal surface. In one embodiment, the output image is made of pixels, with conventional image data (e.g., RGB data) for each pixel but also including depth information for each pixel.

The depth-disparity relationship is illustrated in FIGS. 7-8. The plenoptic image captured by the plenoptic opthalmic camera can be expressed as a four-dimensional light field $I(x,y,u,v)$, where $(x,y)$ are image coordinates and $(u,v)$ are viewpoint coordinates. The light field image $I(x,y,u1,v1)$ is the image as a function of $(x,y)$ that would be observed from the viewpoint $(u1,v1)$.

As illustrated in FIGS. 7A-7D, two-dimensional slices $I(x,u)$ of the light field exhibit a line structure inherent to the characteristics of light fields with uniformly spaced viewpoints. The angle of the line in the $(x,u)$ domain corresponds to different depths in the scene. FIG. 7A illustrates two objects 710 and 720 which are at different depths. Object 720 is forward of object 710. It may or may not occlude object 710, depending on the viewpoint u.

FIG. 7A is taken from viewpoint u1. From this viewpoint, object 710 occupies the x interval 711 and object 720 occupies the x interval 721. The two intervals 711 and 721 do not overlap and there is no occlusion. FIG. 7D illustrates a two-dimensional $(x,u)$ slice of the light field for these two objects. The x-slice of FIG. 7A is marked by u1 on the vertical u axis. The two intervals 711 and 721 are reproduced as the two line segments at coordinate u=u1 in FIG. 7D.

FIG. 7B illustrates the same two objects from a different viewpoint u2. From this viewpoint, object 710 occupies the x interval 712 and object 720 occupies the x interval 722. This is also shown by the two line segments at coordinate u=u2 in FIG. 7D. Note that there is a shift of these segments with respect to the segments at coordinate u=u1. This relative shift due to viewpoint change is a result of parallax or disparity. In FIG. 7B, the two x intervals 712 and 722 are just touching. FIG. 7C illustrates the two objects from viewpoint u3. Here, object 710 occupies the x interval 713 and object 720 occupies the x interval 723, as also shown by the two line segments at u=u3 in FIG. 7D. The two x intervals 713 and 723 are overlapping, which means that object 720 occludes part of object 710. The occluded region is the area of overlap. Repeating this process for other viewpoints u results in the two trapezoids 719 and 729 shown in FIG. 7D, which will be referred to as ray regions. The area of overlap 739 represents the occlusion of object 710 by object 720.

FIG. 7D illustrates an inherent line structure. That is, each point in an object creates a line in the (x,u) plane at an angle φ with respect to the normal to the x axis. A set of adjacent points at the same depth creates a ray region of a certain width, which forms an angle φ with the vertical axis. These angles are labeled φ1 and φ2 in FIG. 7D. In the general four-dimensional case, these angles would be with respect to the normal to the (x,y) plane. For convenience, the angle φ will be referred to as the disparity angle. The disparity angle φ is a measure of disparity and depends on the depth location of the object. Due to parallax, objects that are farther in depth from the viewpoint u-plane produce lines with a smaller disparity angle φ (assuming that the camera is focused to infinity). Ray region 719, which corresponds to object 713 which is farther from the u axis has a lower disparity angle φ. Ray region 729, which corresponds to object 723 which is closer to the u axis, has a larger disparity angle φ. In some configurations of plenoptic cameras, the angle φ can also be negative. These ray regions correspond to objects that are located further along the direction towards the viewpoint, than objects that produce vertical ray regions (i.e., ray regions with φ=0). Generally, the angle φ can take values within the interval (−π/2, π/2).

FIG. 8 illustrates an (x,u) slice from a light field for a grayscale scene. FIG. 8 also illustrates three ray regions 819, 829 and 839, of varying angle (which corresponds to varying depth) and width.

There is a one-to-one mapping between disparity angle φ and depth value z. This mapping depends on the configuration of the plenoptic opthalmic camera and typically also varies as a function of field position (i.e., as a function of (x,y) coordinates). The depth-disparity mapping can be obtained by a calibration process. In one approach, the mapping is fitted into a linear model:

$$\varphi(x,y,z)=a(x,y)z+b(x,y), \quad (3)$$

where a(x, y) and b(x, y) are the mapping coefficients in units of radians/mm and radians, respectively. Further example techniques for obtaining a depth map from a plenoptic image are described in U.S. patent application Ser. No. 14/064,090, "Processing of Light Fields by Transforming to Scale and Depth Space," which is incorporated herein by reference.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

What is claimed is:

1. A method for constructing an optical model of an individual's eye using a plenoptic opthalmic camera, the method comprising:
   the plenoptic opthalmic camera capturing in vivo a plenoptic image of a corneal anterior surface of the individual's eye;
   the plenoptic opthalmic camera operating as a wavefront sensor to measure in vivo a wavefront produced by the individual's eye; and
   generating the optical model of the individual's eye, wherein the optical model of the individual's eye includes optical models of the corneal anterior surface of the individual's eye, of a lens anterior surface of the individual's eye, and of a lens posterior surface of the individual's eye; and generating the optical models comprises:
      generating the optical model for the corneal anterior surface of the individual's eye based on the captured plenoptic image; and
      generating the optical models for the lens anterior surface and for the lens posterior surface of the individual's eye based on the measured wavefront and based on the optical model for the corneal anterior surface.

2. The method of claim 1 wherein the optical models of the corneal anterior surface, of the lens anterior surface, and of the lens posterior surface are each expressed using Zernike polynomials.

3. The method of claim 1 wherein the optical models of the corneal anterior surface, of the lens anterior surface, and of the lens posterior surface are each expressed in a format suitable for use with optical design software.

4. The method of claim 1 wherein generating the optical model of the corneal anterior surface of the individual's eye comprises:
   calculating a disparity map for the captured plenoptic image; and
   generating a depth map of the corneal anterior surface based on the disparity map.

5. The method of claim 4 wherein capturing in vivo the plenoptic image of the corneal anterior surface comprises:
   illuminating the corneal anterior surface with a predefined pattern; and
   the plenoptic opthalmic camera capturing the plenoptic image of the corneal anterior surface as illuminated by the predefined pattern.

6. The method of claim 4 wherein generating a depth map of the corneal anterior surface based on disparity in the captured plenoptic image of the corneal anterior surface comprises:
   calibrating a depth-disparity mapping for the plenoptic opthalmic camera; and
   generating the depth map of the corneal anterior surface based on the calibrated depth-disparity mapping.

7. The method of claim 1 wherein generating the optical models for the lens anterior surface and for the lens posterior surface of the individual's eye based on the measured wavefront and based on the optical model for the corneal anterior surface comprises:
   creating a computer simulation of the individual's eye, the computer simulation including the generated optical model for the corneal anterior surface, and optical models for the lens anterior surface and for the lens posterior surface;
   using the computer simulation to simulate a wavefront produced by the individual's eye; and
   optimizing the optical models for the lens anterior surface and for the lens posterior surface to reduce a difference between the simulated wavefront and the measured wavefront.

8. The method of claim 1 wherein measuring in vivo the wavefront produced by the individual's eye comprises:
   illuminating the individual's eye to produce a point image on a retina of the individual's eye; and the plenoptic opthalmic camera operating as a wavefront sensor to measure in vivo the wavefront produced by the point image reflected from the retina of the individual's eye.

9. A single imaging platform for making in vivo measurements of an individual's eye, the measurements sufficient to construct an optical model of the individual's eye, the single imaging platform comprising:
an illumination module for illuminating the individual's eye; and
a plenoptic opthalmic camera for acquiring measurements of the individual's eye illuminated by the illumination module;
wherein the illumination module and the plenoptic opthalmic camera are configurable for:
a first configuration in which the plenoptic opthalmic camera captures in vivo a plenoptic image of a corneal anterior surface of the individual's eye; and
a second configuration in which the plenoptic opthalmic camera operates as a wavefront sensor to measure in vivo a wavefront produced by the individual's eye; and
a post-processing module that generates the optical model of the individual's eye, wherein the optical model of the individual's eye includes optical models of the corneal anterior surface of the individual's eye, of a lens anterior surface of the individual's eye, and of a lens posterior surface of the individual's eye; and generating the optical models comprises:
generating the optical model for the corneal anterior surface of the individual's eye based on the captured plenoptic image; and
generating the optical models for the lens anterior surface and for the lens posterior surface of the individual's eye based on the measured wavefront and based on the optical model for the corneal anterior surface.

10. The single imaging platform of claim 9 wherein, in the first configuration, the illumination module illuminates the corneal anterior surface with a predefined pattern, and the plenoptic opthalmic camera captures the plenoptic image of the corneal anterior surface as illuminated by the predefined pattern.

11. The single imaging platform of claim 9 wherein, in the second configuration, the illumination module produces a point image on a retina of the individual's eye, and the plenoptic opthalmic camera operates as a wavefront sensor to measure in vivo the wavefront produced by the point image reflected from the retina of the individual's eye.

12. The single imaging platform of claim 9 further comprising:
a beamsplitter positioned to allow simultaneous illumination of the individual's eye by the illumination module and acquisition of measurements by the plenoptic opthalmic camera.

13. The single imaging platform of claim 12 wherein the beamsplitter rejects light that is specularly reflected from the cornea and passes light that is scattered from the cornea.

14. A non-transitory computer-readable storage medium storing executable computer program instructions for constructing an optical model of an individual's eye using measurements captured by a plenoptic opthalmic camera, the instructions executable by a computer system and causing the computer system to perform a method comprising:
accessing a plenoptic image of a corneal anterior surface of the individual's eye, the plenoptic image captured in vivo by a plenoptic opthalmic camera;
accessing a measurement of a wavefront produced by the individual's eye, the wavefront measured in vivo by the plenoptic opthalmic camera operating as a wavefront sensor; and
generating the optical model of the individual's eye based on the captured plenoptic image and the measured wavefront, wherein the optical model of the individual's eye includes optical models of the corneal anterior surface of the individual's eye, of a lens anterior surface of the individual's eye, and of a lens posterior surface of the individual's eye; and generating the optical models comprises:
generating the optical model for the corneal anterior surface of the individual's eye based on the captured plenoptic image; and
generating the optical models for the lens anterior surface and for the lens posterior surface of the individual's eye based on the measured wavefront and based on the optical model for the corneal anterior surface.

15. The non-transitory computer-readable storage medium of claim 14 wherein the optical models of the corneal anterior surface, of the lens anterior surface, and of the lens posterior surface are each expressed using Zernike polynomials.

16. The non-transitory computer-readable storage medium of claim 14 wherein the optical models of the corneal anterior surface, of the lens anterior surface, and of the lens posterior surface are each expressed in a format suitable for use with optical design software.

17. The non-transitory computer-readable storage medium of claim 14 wherein generating the optical model of the corneal anterior surface of the individual's eye comprises:
calculating a disparity map for the captured plenoptic image; and
generating a depth map of the corneal anterior surface based on the disparity map.

18. The non-transitory computer-readable storage medium of claim 17 wherein generating a depth map of the corneal anterior surface based on disparity in the captured plenoptic image of the corneal anterior surface comprises:
calibrating a depth-disparity mapping for the plenoptic opthalmic camera; and
generating the depth map of the corneal anterior surface based on the calibrated depth-disparity mapping.

19. The non-transitory computer-readable storage medium of claim 14 wherein generating the optical models for the lens anterior surface and for the lens posterior surface of the individual's eye based on the measured wavefront and based on the optical model for the corneal anterior surface comprises:
creating a computer simulation of the individual's eye, the computer simulation including the generated optical model for the corneal anterior surface, and optical models for the lens anterior surface and for the lens posterior surface;
using the computer simulation to simulate a wavefront produced by the individual's eye; and
optimizing the optical models for the lens anterior surface and for the lens posterior surface to reduce a difference between the simulated wavefront and the measured wavefront.

20. The single imaging platform of claim 9 wherein the optical models of the corneal anterior surface, of the lens anterior surface, and of the lens posterior surface are each expressed in a format suitable for use with optical design software.

* * * * *